(12) United States Patent
Morley et al.

(10) Patent No.: US 8,800,708 B2
(45) Date of Patent: Aug. 12, 2014

(54) DEVICE AND PROCESS FOR GIVING A BREATH SAMPLE WITH A BREATH ALCOHOL INTERLOCK DEVICE

(71) Applicant: Dräger Safety AG & Co. KGaA, Lübeck (DE)

(72) Inventors: Stefan Morley, Lübeck (DE); Martin Zimmermann, Hamburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 13/714,712

(22) Filed: Dec. 14, 2012

(65) Prior Publication Data

US 2013/0277134 A1    Oct. 24, 2013

(30) Foreign Application Priority Data

Apr. 24, 2012   (DE) .......................... 10 2012 008 165

(51) Int. Cl.
*B60K 28/04*          (2006.01)

(52) U.S. Cl.
USPC ........................................................ 180/272

(58) Field of Classification Search
USPC ............... 73/23.3; 180/272, 279; 340/426.11, 340/576; 701/45
See application file for complete search history.

(56) References Cited

U.S. PATENT DOCUMENTS

| | | | | |
|---|---|---|---|---|
| 5,020,628 A * | 6/1991 | Bigliardi et al. | ............... | 180/272 |
| 5,426,415 A * | 6/1995 | Prachar et al. | ................ | 340/576 |
| 6,853,956 B2 * | 2/2005 | Ballard et al. | ................ | 702/183 |
| 7,481,292 B2 * | 1/2009 | Mobley et al. | ................ | 180/272 |
| 7,934,577 B2 * | 5/2011 | Walter et al. | ................... | 180/272 |
| 8,179,271 B2 * | 5/2012 | Kamiki | ......................... | 340/576 |
| 2004/0088096 A1 | 5/2004 | Stock et al. | | |
| 2005/0230175 A1 | 10/2005 | Brown et al. | | |
| 2010/0294583 A1 | 11/2010 | Biondo et al. | | |

FOREIGN PATENT DOCUMENTS

| | | |
|---|---|---|
| DE | 102 51 281 B3 | 6/2004 |
| DE | 10 2010 020 857 A1 | 1/2011 |
| EP | 1 874 580 B1 | 3/2011 |
| EP | 2360048 A2 | 8/2011 |
| JP | 2009-018712 A | 1/2009 |
| WO | 94/22686 A1 | 10/1994 |

* cited by examiner

*Primary Examiner* — Faye M Fleming
*Assistant Examiner* — Robert A Coker
(74) *Attorney, Agent, or Firm* — McGlew and Tuttle, P.C.

(57) ABSTRACT

A device for preventing a vehicle from being started includes a breath gas analyzer (5), which is arranged within the vehicle and is designed to detect the breath alcohol content of an operator. A repeated test can be performed, without compromising the operator, with a control unit (1), which is connected to the breath gas analyzer (5), a motion sensor (4) and an ignition system (3) of the vehicle, to request a breath alcohol test at presettable times $t_W$ in such a way that the breath alcohol test is performed with the vehicle stopped. The control unit (1) is also designed to preset, beginning from the time $t_W$, a time interval as a latency period $t_L$ within which the vehicle must be stopped.

12 Claims, 5 Drawing Sheets

DEVICE AND PROCESS FOR GIVING A BREATH SAMPLE WITH A BREATH ALCOHOL INTERLOCK DEVICE

CROSS REFERENCE TO RELATED APPLICATIONS

This application claims the benefit of priority under 35 U.S.C. §119 of German Patent Application DE 10 2012 008 165.0 filed Apr. 24, 2012, the entire contents of which are incorporated herein by reference.

FIELD OF THE INVENTION

The present invention pertains to a device and a process for giving a breath sample with a breath alcohol interlock device.

BACKGROUND OF THE INVENTION

An interlock is an alcohol-measuring device with a vehicle immobilizer in a motor vehicle. According to the current state of the art, the alcohol measurement is carried out as a breath alcohol measurement. However, this is not a necessary condition for an interlock system, but other breath alcohol measurements may also be used, in principle, for the system being described here. The goal of an interlock is to prevent a driver who is under the influence of alcohol from starting the vehicle engine. The interlock device can be installed in the motor vehicle in a simple manner. By installing an interlock, accidents related to alcohol can be prevented from occurring. Furthermore, it is suitable for supporting long-term behavioral changes in handling alcohol. Interlock devices are often installed in vehicles later. This is done either for a certain time period or for the remaining service live of the vehicle.

The practical procedure is, in general, such that the driver of the vehicle is prompted by the interlock to perform a breath alcohol measurement when he is attempting to start the vehicle. Depending on the result of this measurement, the signal chain for starting the engine is then released and the driver of the vehicle is enabled to start the engine. To improve the tamperproofness of the interlock concept, it is, furthermore, common practice that the driver of a vehicle equipped with an interlock system has to give another breath sample after some time. It is ensured by this, for example, that the first sample was not given by another person.

A device for the repeated giving of a breath sample is known from EP 1 874 580 B1.

To perform a repeated test, the driver is prompted after a time $t_W$ to give another breath sample. This shall ensure that the person who gave the first sample is also the driver of the vehicle and that no alcohol was consumed during travel. This time $t_W$ is determined such that it is a time interval after the last test within which the time $t_W$ is calculated according to the random principle. An active alcohol test and a passive alcohol test are used for this. A passive test is an alcohol test during which the driver of the vehicle does not blow directly into the device, i.e., he does not perform an active test, but the device automatically takes a gas sample. However, it happens in practice that repeated tests are performed, in general, during travel, i.e., the vehicle is not stopped.

Giving a breath sample into an interlock breath alcohol-measuring device means that it is absolutely necessary to blow into the mouthpiece of a hand-held device, i.e., to bring this hand-held device to the mouth with at least one hand in order to then give this sample. Furthermore, it is common to display the result of the measurement as, e.g., "Bestanden"/"Nicht Bestanden" or "Pass"/"Fail" on the display of the hand-held device. If the criteria for an acceptable breath sample are not met, i.e., blowing time too short, blowing too weak or incorrect use of a breathing technique, blowing and sucking, and blowing with a humming noise, this is usually also displayed on the display and a repeated breath sample is requested. The display must also be watched for this, and driver of the vehicle would thus be distracted from the traffic proper.

There are often limitations for similar actions in the vehicle. Thus, there often are provisions in the laws that prohibit, in principle, the use of a telephone for the vehicle driver while driving unless at least a so-called hands-free unit is used. Such a device enables the vehicle driver to use his telephone without holding the cell phone at the ear with at least one hand.

Recognition of the state of motion of a vehicle is known from DE 102 51 281 B3. This document shows a process for recognizing the motion of a motor vehicle, in which an unacceptable bypassing of blocking, e.g., by pushing, is detected by means of an acceleration sensor.

SUMMARY OF THE INVENTION

A basic object of the present invention is to provide a device and a process with which it shall be ensured that the repeated test can be performed without compromising the operator (driver).

According to the invention, a device for preventing a vehicle from being started is provided. The device comprises a breath gas analyzer arranged within the vehicle and detecting a breath alcohol content of an operator (driver) of the vehicle during a breath alcohol test. A sensor is provided for detecting motion of the vehicle. A control unit is connected to the breath gas analyzer and connected to an ignition system of the vehicle. The control unit compares a breath alcohol level detected with a threshold value and acts on the ignition system in case of a detected breath alcohol level higher than or equal to the threshold value such that ignition of the vehicle is prevented from occurring. The sensor is connected to the control unit. The control unit requests the breath alcohol test at presettable times in such a way that the breath alcohol test is performed with the vehicle stopped, wherein the control unit has a preset time interval as a latency period, beginning from the presettable times, within which the vehicle must be stopped.

Provisions are made according to the present invention for the repeated tests having to be performed, beginning from the preset times $t_W$, within the preset latency period $t_L$ in order for these repeated tests to be able to be considered valid breath tests. The vehicle driver shall at the same time have the opportunity to stop the vehicle within the latency period $t_L$ and to give the sample with the vehicle stopped.

To recognize the state of motion of the vehicle, it is possible to install in the vehicle a sensor, which detects the state of motion of the vehicle. In a first possible embodiment, this sensor is integrated in the control device of the interlock system, and it is connected to the control device of the interlock system by a digital or analog interface in a second possible embodiment. In a preferred embodiment, the motion sensor is an acceleration sensor, as it is available commercially as a so-called three-axis sensor. In an alternative embodiment, the motion sensor is a receiver of a satellite-supported navigation system, for example, GPS, which may internally also be expanded by an acceleration sensor and a compass.

Another alternative solution is obtained by the use of a sensor that is already integrated in the vehicle and determines the state of motion of the vehicle. This sensor is connected to the control device of the interlock system by a digital or analog interface. In a preferred embodiment, the motion sensor is a tachometer of the vehicle, as it can be read, for example, by the CAN interface, e.g., at the OBD II port.

First Measuring Process

A first possible preferred measuring process for a travel with a vehicle, in which a breath alcohol interlock is installed, can be described as follows:

After the driver has started the vehicle at first by giving a favorable breath sample, which showed no alcohol concentration above the preset limit, the interlock system determines the time $t_W$ as a random value from the minimum time $t_{min}$ preset as a parameter and the maximum time $t_{max}$, which is likewise preset as a parameter. One possible manner of determining the time $t_W$ is to set the time according to the random principle as a time between $t_{min}$ and $t_{max}$. One should proceed such that $t_{min}$ is measured beginning from the last test. This test was either the first test or a repeated test itself. The interlock system will then prompt the driver of the vehicle at the time $t_W$ to give a new breath sample and to stop the vehicle for doing so.

The driver is usually given a latency period $t_L$ to give the breath sample into the hand-held device of the interlock system. If the breath alcohol sample is not given within this time $t_L$, this can be stored as a violation of the rules in the log of the interlock system. If the vehicle has not stopped within the time $t_L$, this is likewise stored in the log. If the driver gives the breath sample within the time $t_L$, the breath sample is analyzed. The vehicle will then have two possible relevant states. The first relevant state is that the vehicle had been stopped during the giving of the breath sample, which was determined, for example, by the vehicle-independent sensor. This is now a valid breath sample. The result of this breath sample as well as the validity of the giving are stored in the log of the interlock system. The second relevant state is that in which the vehicle was in motion during the giving of the breath sample. This is an invalid breath sample in this case. Depending on the parametrization of the interlock system, the measured value for the breath sample may be stored in the log of the interlock system, and the fact that the breath sample was given with the vehicle in motion is documented as well.

The result of the breath test is not displayed to the driver in a first variant of the first measuring process. In a second variant, it is displayed to the driver of the vehicle that the attempt to give a breath sample was invalid. It is displayed to him, in particular, that the vehicle was in motion at the time of giving of the breath sample.

Second Measuring Process

A second possible preferred measuring process during the travel of a vehicle, in which a breath alcohol interlock is installed, pertains to the use of a navigation system and can be described as follows:

After the driver had started the vehicle at first by giving a valid breath sample, which did not have an alcohol concentration above the preset limit, the interlock system determines the time $t_W$ as a random value from the minimum time $t_{min}$ preset as a parameter and the maximum time $t_{max}$, which is likewise preset as a parameter. A possible manner of determining the time $t_W$ is to set this time according to the random principle as time between $t_{min}$ and $t_{max}$. One should proceed such that $t_{min}$ is measured beginning from the last test. This test was either the first test or a repeated test itself. At time $t_W$, the interlock system will then prompt the driver of the vehicle to give another breath sample and to stop the vehicle for this.

The driver is given the latency period $t_L$ to give the breath sample into the hand-held device of the interlock system. The time $t_L$ is determined by means of the navigation system in this second possible measuring process. $t_L$ is calculated as the sum of a parametrized minimum latency period $t_{L0}$ and the time elapsing during travel according to the regulations to a nearest stopping place when the vehicle is, e.g., on a turnpike or throughway at the time the driver was prompted to perform a repeated test;

a multiple of the time during travel according to the regulations until leaving a tunnel or a bridge if the vehicle is in a tunnel or on a bridge at the time the driver was prompted to perform a repeated test;

a time period depending on the type of road, where the type of road may be a street in the downtown or a street or road outside the downtown;

as well as a possible additional latency period offset $t_L$, off. If the breath alcohol sample is given outside the latency period $t_L$, this may be stored in the log of the interlock system as a violation of the rules.

If a satellite-supported navigation system, which may also be expanded internally by an acceleration sensor and a compass, is used as the motion sensor, the navigation system may be installed either permanently in the vehicle or temporarily in the vehicle. The interlock system documents whether the vehicle has come to a stop within the time $t_L$. If this is not the case, this fact is stored in the log of the interlock system. It is also documented whether the driver of the vehicle has stopped the vehicle at one of the nearest possible locations. This is achieved by comparing the route traveled with the maps being stored in the navigation system.

If the vehicle has stopped within the time $t_L$, this is likewise stored in the log. If the driver gives the breath sample within the time $t_L$, there are two possible relevant states of the vehicle. The first relevant state is that the vehicle was stopped during the giving of the breath sample, which was determined, e.g., by the vehicle-independent sensor. This is now a valid breath sample. The result for this breath sample is stored, just like the validity of the giving, in the log of the interlock system. The second relevant state is that in which the vehicle was moving during the giving of the breath sample. The breath sample is not a valid one in this case. Depending on the parametrization of the interlock system, the measured value for the breath sample may be stored in the log of the interlock system, and the fact that the breath sample was given while the vehicle was moving is documented as well.

The result for the breath sample, in this case the result of giving a sample during travel, is not displayed to the driver. However, it is displayed to the driver of the vehicle that the attempt to give a breath sample was an invalid one. It is displayed to him, in particular, that the vehicle was moving at the time of giving of the breath sample.

An alternative within the second preferred measuring process is that the interlock system prompts the driver at the time $t_W$ to stop the vehicle in order to give another breath sample. As long as the vehicle is not stopped, the breath sample is not accepted in this alternative. This means that either no measurement is performed or the measurement is not analyzed or the measurement is analyzed and the result is discarded. It is displayed to the driver of the vehicle that the attempt to give a breath sample was an invalid one. It is displayed to him, in particular, that the vehicle was in motion at the time of giving of the breath sample. If it is determined by the vehicle-independent sensor that the vehicle was stopped, the actual breath sample is requested. This will then be a valid breath sample. The result for this breath sample as well as the validity of the giving will be stored in the log of the interlock system.

The coupling with the navigation system can be used to recognize whether the driver of the vehicle has actually taken advantage of the next possibility to stop within the latency period $t_L$ relative to the time at which he had been requested to do so or whether he has passed that possibility.

The process according to the present invention for preventing a vehicle from being started is carried out with a device, which has a breath gas analyzer, which is arranged within the vehicle and is designed to detect the breath alcohol content of an operator and has a control unit, which is connected to the breath gas analyzer and an ignition system of the vehicle and is designed to compare the breath alcohol level detected with a threshold value and is configured to actuate the ignition system in case of a detected breath alcohol level higher than or equal to the threshold value such that ignition of the vehicle is prevented, and it has a sensor for detecting motion of the vehicle, which is connected to the control unit. The process is characterized by the following steps: the control unit is designed to request another breath alcohol test at presettable times $t_W$, which follow a first step, in such a way that the breath alcohol test is performed with the vehicle stopped, wherein the control unit is designed, furthermore, to preset, starting from the times $t_W$, a time interval as a latency period $t_L$ within which the vehicle must be brought to a stop.

Provisions are advantageously made for designing the sensor as a satellite-supported navigation system and for dynamically adapting the latency period $t_L$ to the presence of possible stopping places.

One exemplary embodiment of the device according to the present invention is shown in the drawings and will be explained in more detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
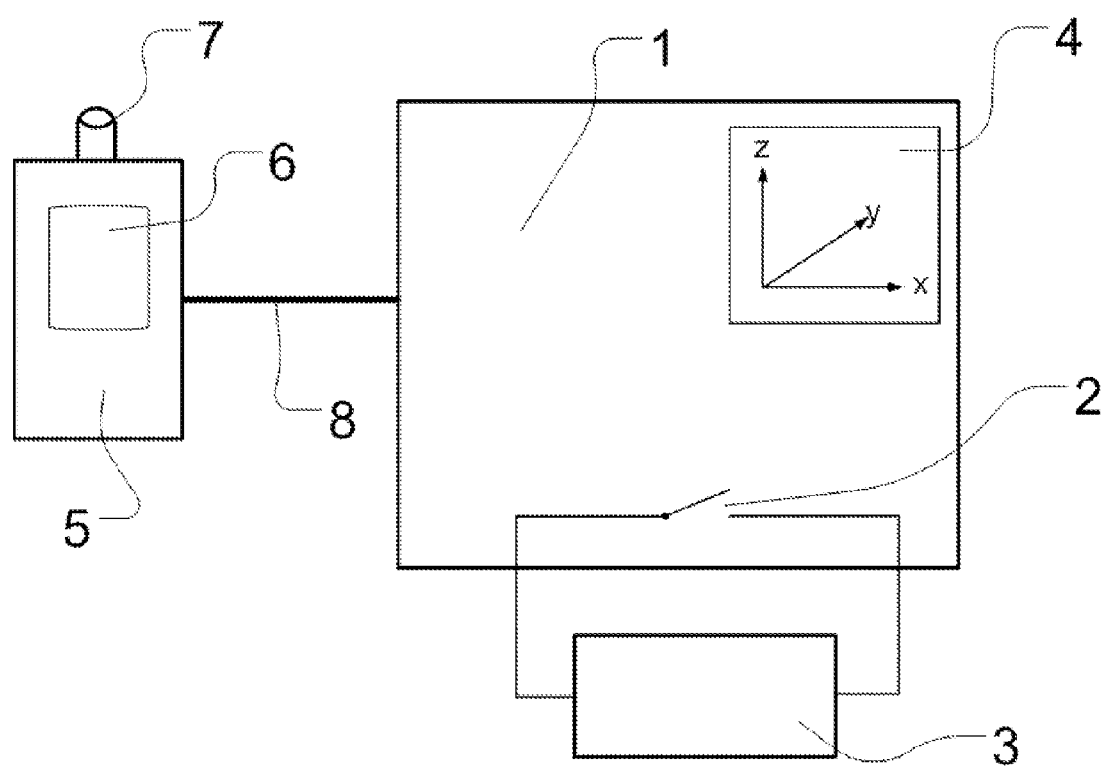
FIG. 1 is schematic view showing a first embodiment with internal acceleration sensor.
Figure 4:
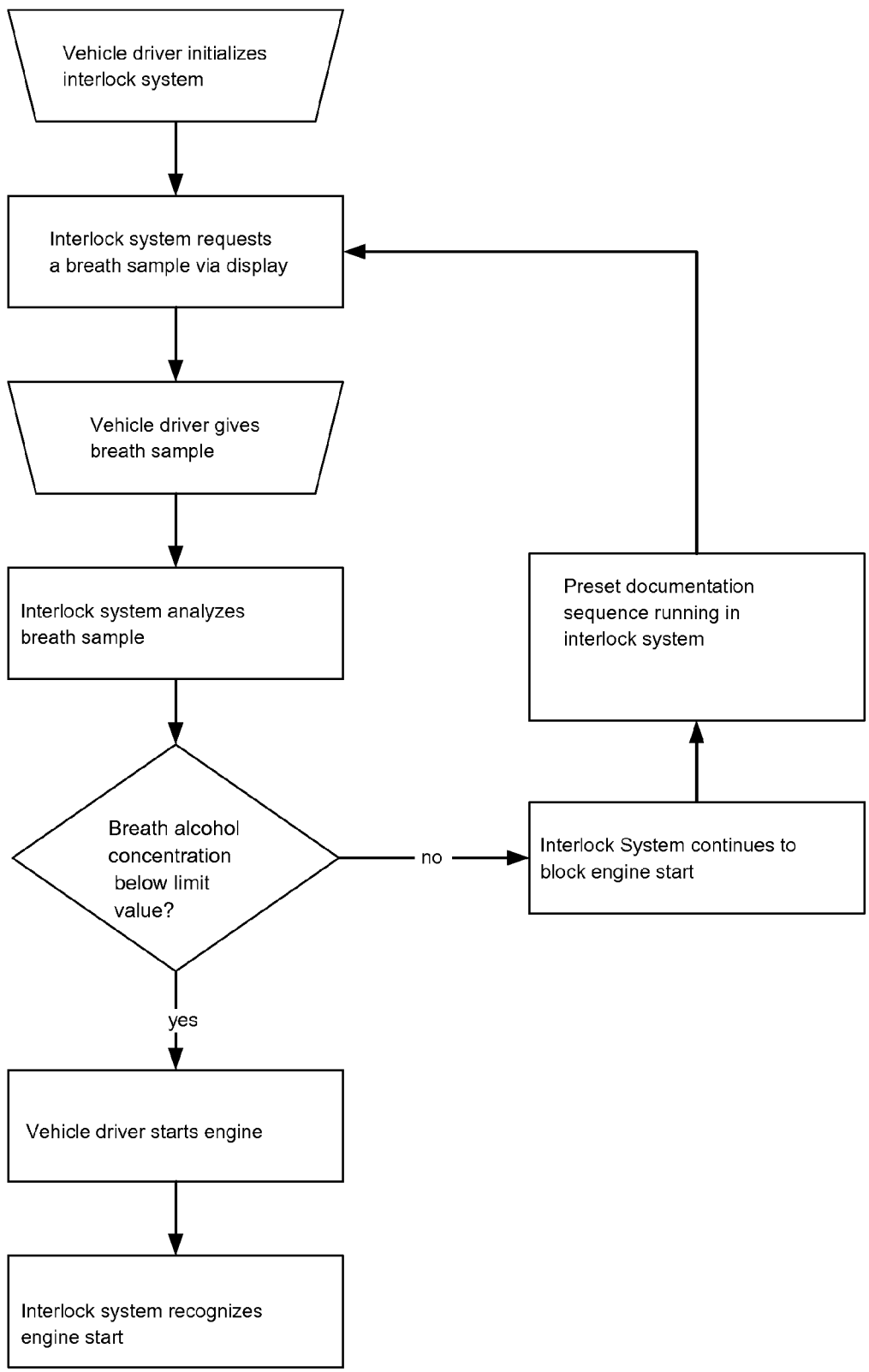
FIG. 4 is a diagram showing an engine start process.

Referring to the drawings in particular, in the first preferred embodiment corresponding to FIG. 1, the interlock system operates such that a control unit 1 is integrated in the vehicle circuit before starting the internal combustion engine or before releasing an electric motor such that release takes place only by closing a contact 2, which closes a starter circuit 3 in case of an internal combustion engine, so that the engine can be started. It is necessary for this for the driver of the vehicle to have given a breath sample into the breath alcohol-measuring device 5, which is equipped with a display unit 6 and is connected to the control unit 1 via a wired or wireless data line 8. The driver of the vehicle blows for this into a mouthpiece 7. If the breath alcohol concentration is below the preset limit value, the contact shown as an open switch in the figure is closed by the control unit 1 and starting of the engine is enabled. This process is schematic ally illustrated in FIG. 4.

Figure 2:
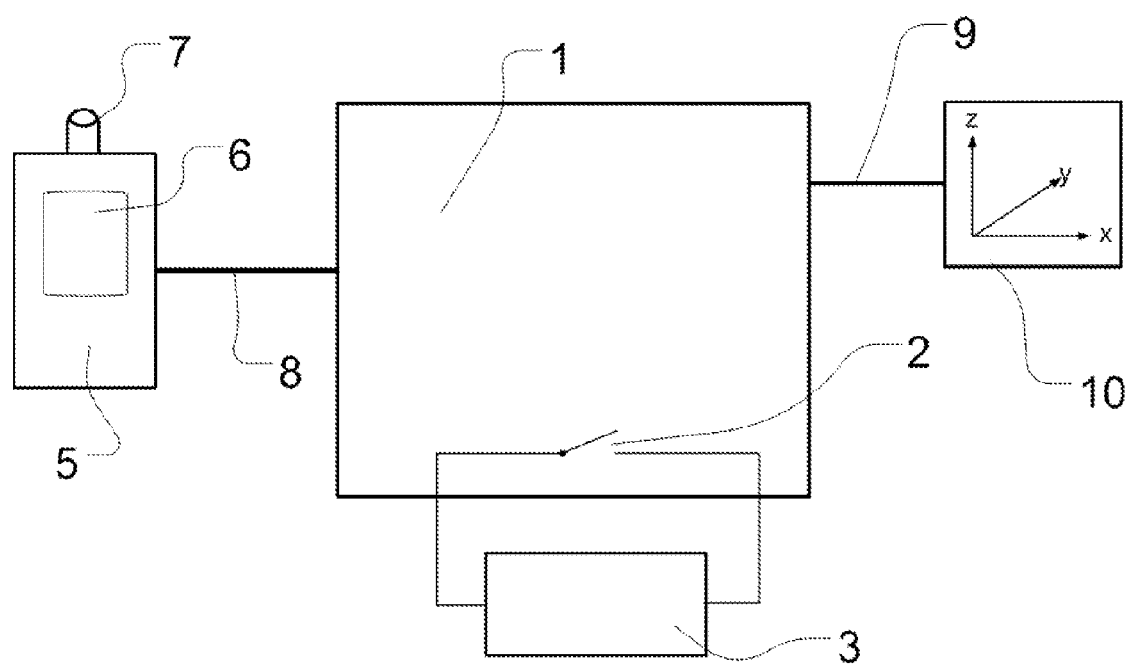
FIG. 2 is schematic view showing a second embodiment with a navigation system.

Unlike in the first preferred embodiment, an external sensor 10, which is connected to the control unit 1 via at least one wired or wireless data line 9, FIG. 2, can be used in a second embodiment to recognize whether the vehicle was moving or stopped at the time of a repeated breath sample. This external sensor 10 can obtain the information on the state of motion of the motor vehicle from a satellite-supported navigation system, for example, GPS. Identical components are designated by the same reference numbers as in FIG. 1.

Figure 3:
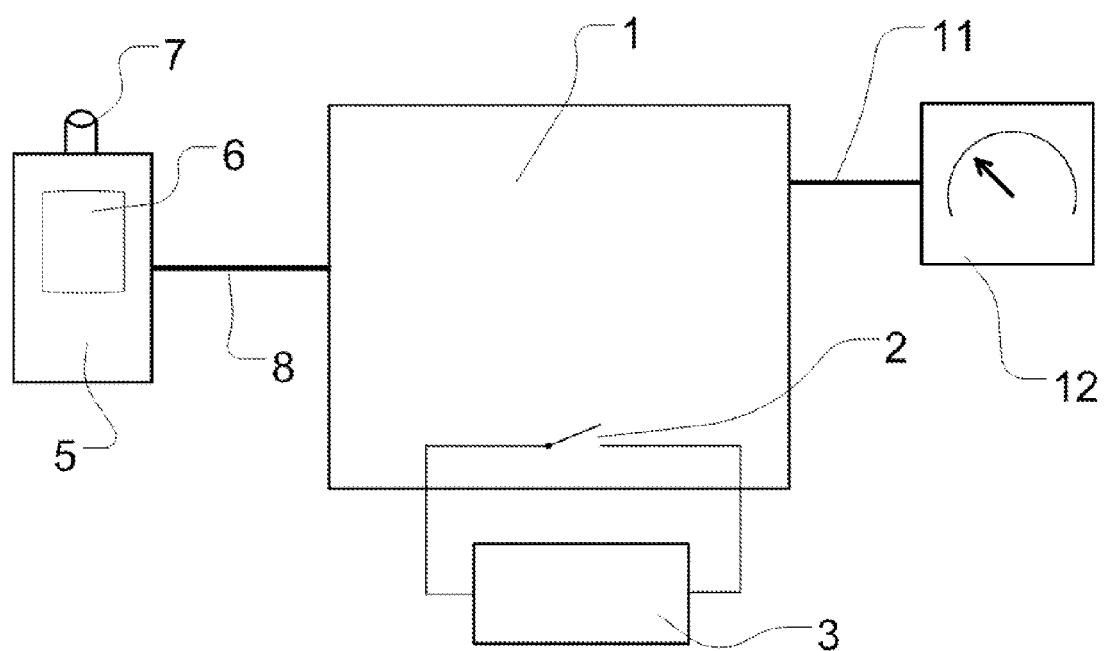
FIG. 3 is schematic view showing a third embodiment with a tachometer transducer.

In a third preferred embodiment corresponding to FIG. 3, a tachometer transducer 12, which is connected to the control unit 1 via at least one wired or wireless data line 11, is used to recognize whether the vehicle was moving or stopped at the time of a repeated breath sample.

Figure 5:
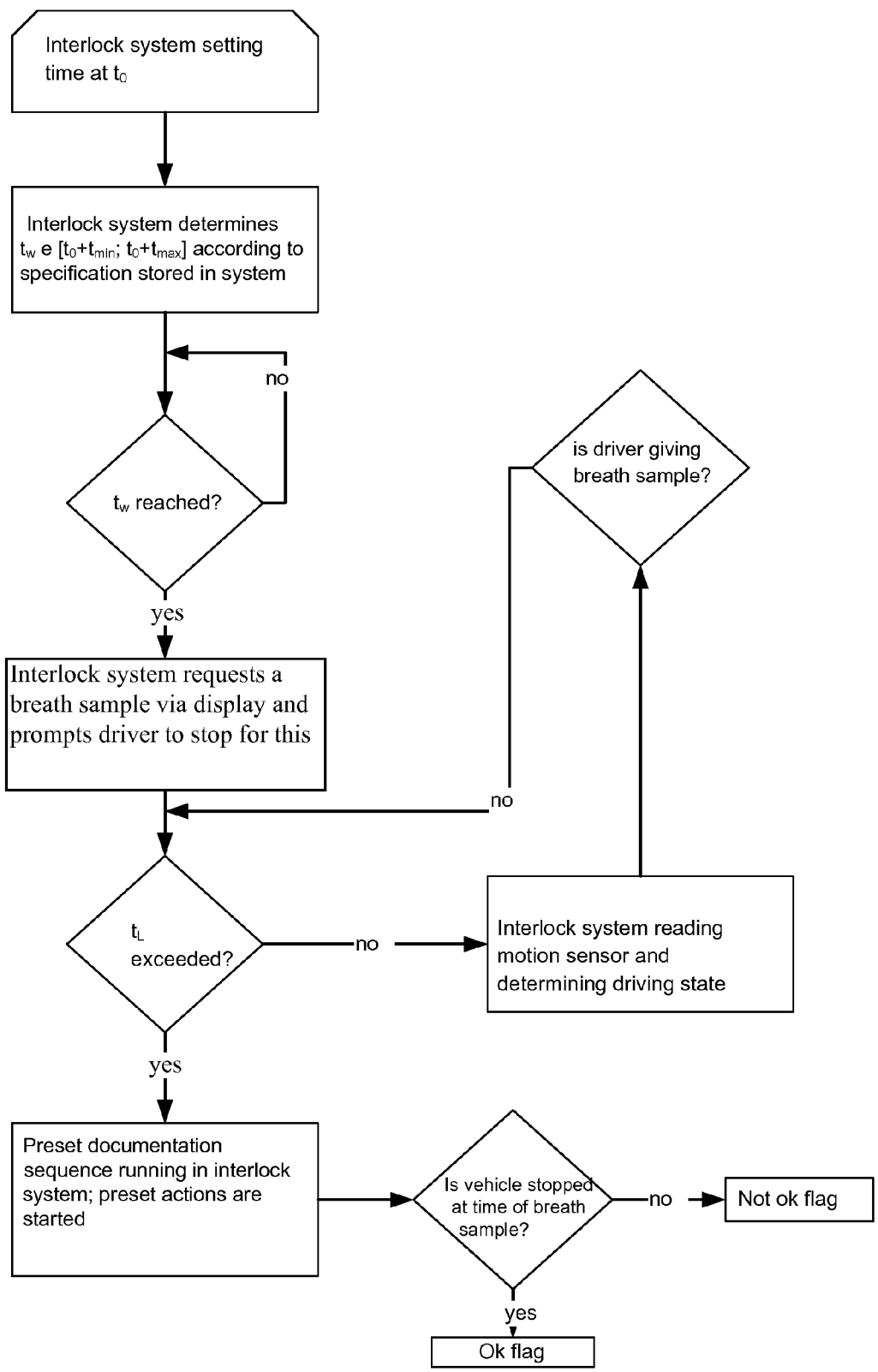
FIG. 5 is a diagram showing a repeated test procedure.

FIG. 5 illustrates a repeated test procedure. At the time of the repeated test ("rolling retest"), it is signaled to the vehicle driver via a display unit 6 of the hand-held breath alcohol-measuring device (handset) 6 that a repeated breath sample is to be given. The vehicle driver will then have to give another breath sample within a time $t_L$. This additional breath sample is used, among other things, to check whether the driver of the vehicle had given the first sample himself or whether the first sample was given by another person instead of the vehicle driver, who is under the influence of alcohol. It can also be determined whether the driver of the vehicle consumed alcohol while driving. The acceleration sensor 4 integrated in the control unit 6 now determines in the first preferred embodiment whether the vehicle was stopped or moving at the time of giving of the breath sample. Depending on the state of motion of the vehicle, an algorithm integrated in the electronic circuit of the control unit makes a decision about the validity of sample giving and the documentation of the operation by setting a flag for OK or Not OK.

While specific embodiments of the invention have been shown and described in detail to illustrate the application of the principles of the invention, it will be understood that the invention may be embodied otherwise without departing from such principles.

APPENDIX

| LIST OF REFERENCE NUMBERS | |
|---|---|
| 1 | Control unit |
| 2 | Contact |
| 3 | Starter circuit |
| 4 | Acceleration sensor |
| 5 | Breath alcohol-measuring device |
| 6 | Display unit |
| 7 | Mouthpiece |
| 8 | Data line |
| 9 | Wireless data line |
| 10 | Navigation system |
| 11 | Wireless data line |
| 12 | Tachometer transducer |

What is claimed is:
1. A device for preventing a vehicle from being started, the device comprising:
a breath gas analyzer arranged within the vehicle and detecting a breath alcohol content of an operator of the vehicle during a breath alcohol test;
a sensor for detecting motion of the vehicle;
a control unit connected to said breath gas analyzer and connected to an ignition system of the vehicle, said control unit comparing a breath alcohol level detected with a threshold value and acting on the ignition system in case of a detected breath alcohol level higher than or equal to the threshold value such that ignition of the vehicle is prevented from occurring, said sensor being connected to said control unit, said control unit requesting the breath alcohol test at presettable times in such a way that said breath alcohol test is performed with the vehicle stopped, wherein said control unit has a preset time interval as a latency period, beginning from the presettable times, within which the vehicle must be stopped.

2. A device in accordance with claim 1, wherein the sensor is an acceleration sensor.

3. A device in accordance with claim 1, wherein said sensor comprises a satellite-supported navigation system and said control unit dynamically adapts the latency period to a presence of possible stopping places.

4. A device in accordance with claim 1, wherein said sensor comprises a tachometer transducer of the vehicle.

5. A process for preventing a vehicle from being started, the process comprising the steps of:
providing a device with a breath gas analyzer arranged within the vehicle and detecting a breath alcohol content of an operator of the vehicle during a breath alcohol test, with a sensor for detecting motion of the vehicle and with a control unit connected to the breath gas analyzer and connected to an ignition system of the vehicle and connected to the sensor;
requesting the breath alcohol test as a first test with the vehicle stopped;
comparing, with the control unit, a breath alcohol level detected, during the breath alcohol test, with a threshold value;
acting on the ignition system, with the control unit, in case of a detected breath alcohol level higher than or equal to the threshold value such that ignition of the vehicle is prevented from occurring;
requesting, with the control unit, further breath alcohol tests at presettable times, which follow the first test, in such a way that each of the breath alcohol tests is performed with the vehicle stopped, wherein the control unit is designed, furthermore, to preset, beginning from the presettable times, a time interval as a latency period within which the vehicle must be stopped.

6. A process in accordance with claim 5, wherein the sensor is designed as a satellite-supported navigation system and the latency period is dynamically adapted to the presence of possible stopping places.

7. A process in accordance with claim 5, wherein the sensor is an acceleration sensor.

8. A process in accordance with claim 5, wherein the sensor comprises a tachometer transducer of the vehicle.

9. A vehicle system comprising:
a vehicle with an ignition system; and
a device for preventing a vehicle from being started, the device comprising:
a breath gas analyzer arranged within the vehicle and detecting a breath alcohol content of an operator of the vehicle during a breath alcohol test;
a sensor for detecting motion of the vehicle;
a control unit connected to said breath gas analyzer and connected to said ignition system of the vehicle, said control unit comparing a breath alcohol level detected with a threshold value and acting on the ignition system in case of a detected breath alcohol level higher than or equal to the threshold value such that ignition of the vehicle is prevented from occurring, said sensor being connected to said control unit, said control unit requesting the breath alcohol test at presettable times in such a way that said breath alcohol test is performed with the vehicle stopped, wherein said control unit has a preset time interval as a latency period, beginning from the presettable times, within which the vehicle must be stopped.

10. A vehicle system in accordance with claim 9, wherein the sensor is an acceleration sensor.

11. A vehicle system in accordance with claim 9, wherein said sensor comprises a satellite-supported navigation system and said control unit dynamically adapts the latency period to a presence of possible stopping places.

12. A vehicle system in accordance with claim 9, wherein said sensor comprises a tachometer transducer of the vehicle.

* * * * *